(12) United States Patent
Ullah et al.

(10) Patent No.: US 6,331,316 B1
(45) Date of Patent: Dec. 18, 2001

(54) ENTERIC COATED PHARMACEUTICAL TABLET AND METHOD OF MANUFACTURING

(75) Inventors: Ismat Ullah, Cranbury; Gary J. Wiley, Jackson, both of NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/549,455

(22) Filed: Apr. 14, 2000

Related U.S. Application Data

(63) Continuation of application No. 09/118,418, filed on Jul. 17, 1998, now abandoned.

(51) Int. Cl.[7] .............................. A61K 9/20; A61K 9/48; A61K 9/32; A61K 31/70
(52) U.S. Cl. ................. 424/482; 424/464; 424/474; 424/475; 424/451; 514/23
(58) Field of Search .................................. 424/464, 468, 424/474, 475, 479, 482, 480, 458, 451, 478; 514/23

(56) References Cited

U.S. PATENT DOCUMENTS

| | | | |
|---|---|---|---|
| 4,432,996 | 2/1984 | Zeitoun et al. | 424/21 |
| 4,524,060 | 6/1985 | Mughal et al. | 424/19 |
| 4,556,552 | 12/1985 | Porter et al. | 424/32 |
| 4,704,295 | 11/1987 | Porter et al. | 424/3 |
| 4,775,536 | 10/1988 | Patell | 424/471 |
| 4,786,505 | 11/1988 | Lovgren et al. | 424/468 |
| 4,794,001 | 12/1988 | Mehta et al. | 424/458 |
| 4,808,413 | 2/1989 | Joshi et al. | 424/458 |
| 4,853,230 | 8/1989 | Lovgren et al. | 424/466 |
| 4,861,759 | 8/1989 | Mitsuya et al. | 514/46 |
| 4,920,210 | 4/1990 | Koszalka et al. | . |
| 4,925,675 | 5/1990 | Giannini et al. | 424/469 |
| 4,975,283 | 12/1990 | Patell | 424/470 |
| 4,994,279 | 2/1991 | Aoki et al. | 424/494 |
| 5,026,559 | 6/1991 | Eichel et al. | 424/458 |
| 5,026,560 | 6/1991 | Makino et al. | 424/494 |
| 5,158,777 * | 10/1992 | Abramowitz et al. | . |
| 5,175,003 * | 12/1992 | Goldman | . |
| 5,225,202 * | 7/1993 | Hodges et al. | . |
| 5,254,539 | 10/1993 | Mitsuya et al. | 514/46 |
| 5,326,570 | 7/1994 | Rudnic et al. | . |
| 5,350,584 | 9/1994 | McClelland et al. | 424/501 |
| 5,422,121 | 6/1995 | Lehmann et al. | . |
| 5,510,114 | 4/1996 | Borella et al. | . |
| 5,536,507 | 7/1996 | Abramowitz et al. | 424/479 |
| 5,556,839 | 9/1996 | Greene et al. | . |
| 5,616,566 | 4/1997 | Mitsuya et al. | 514/47 |
| 5,686,106 | 11/1997 | Kelm et al. | 424/463 |
| 5,733,575 | 3/1998 | Mehra et al. | 424/480 |

FOREIGN PATENT DOCUMENTS

| | | | |
|---|---|---|---|
| 0754452 | 1/1997 | (EP) | A61K/9/52 |
| 0781549 | 7/1997 | (EP) | A61K/9/28 |
| WO94/03160 | 2/1994 | (WO) | . |

OTHER PUBLICATIONS

Ishibashi et al., "Design and Evaluation of a New Capsule–Type Dosage Form for Colon–Targeted Delivery of Drugs", Int'l. J. of Pharmaceutics 168 (1998) pp. 31–40.

C.G. Wilson and Neena Washington, "Small Intestine: Transit and Absorption of Drugs"; Chapter 5—Physiological Pharmaceutics—Biological Barriers to Drugs Absorption; 1989 pp. 71–90.

* cited by examiner

*Primary Examiner*—Thurman K. Page
*Assistant Examiner*—Brian K. Seidleck
(74) *Attorney, Agent, or Firm*—Barry J. Marenberg; Gabriel Lopez

(57) ABSTRACT

A high drug load enteric coated pharmaceutical composition is provided which includes a core in the form of a tablet and which is comprised of a medicament which is sensitive to a low pH environment of less than 3, such as ddl, and having an enteric coating formed of methacrylic acid copolymer and a plasticizer. The tablets may be of varying sizes and may be orally ingested individually or a plurality of tablets sufficient to attain a desired dosage may be encapsulated in a dissolvable capsule. The tablets have excellent resistance to disintegration at pH less than 3 but have excellent drug release properties at pH greater than 4.5. A novel method of making said pharmaceutical composition is also disclosed.

35 Claims, No Drawings

ENTERIC COATED PHARMACEUTICAL TABLET AND METHOD OF MANUFACTURING

This is a continuation of Ser. No. 09/118,418, Jul. 17, 1998, abandoned.

BRIEF DESCRIPTION OF THE INVENTION

The present invention is directed to an enteric-coated pharmaceutical composition in the form of a tablet which comprises an acid labile high drug load medicament, such as ddI, which is sensitive to a low pH environment of less than 3, and which includes an enteric coating such as Eudragit L-30-D 55 and a plasticizer, but which does not require a subcoat. The tablets have excellent resistance to disintegration at pH less than 3 but have excellent drug release properties at pH greater than 4.5. A novel method of making said pharmaceutical composition is also disclosed.

BACKGROUND OF THE INVENTION

Enteric coatings have been used for many years to arrest the release of the drug from orally ingestible dosage forms. Depending upon the composition and/or thickness, the enteric coatings are resistant to stomach acid for required periods of time before they begin to disintegrate and permit slow release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64–71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001).

Most enteric coating polymers begin to become soluble at pH 5.5 and above, with maximum solubility rates at pHs greater than 6.5.

Numerous enteric coated and/or extended release pharmaceutical compositions and the methods of making these compositions have been disclosed in the art. Prior art compositions, however, often comprise numerous extra ingredients in addition to the medicaments, such as fillers, buffering agents, binders and wetting agents, all of which add to the bulk of the composition and reduce the amount of active medicament which can be contained in the composition. The processes for preparing these aforementioned pharmaceutical compositions require multiple time consuming steps, including subcoating and outer coating steps. Furthermore, many of these pharmaceutical compositions are intended for delivery in the lower GI tract, i.e. in the colon, as opposed to the upper intestines, i.e. the duodenum of the small intestine.

U.S. Pat. No. 5,225,202 discloses enteric coated pharmaceutical compositions utilizing neutralized hydroxypropyl methylcellulose phthalate polymer (HPMCP) coating. The pharmaceutical compositions disclosed comprise an acid labile medicament core, a disintegrant, one or more buffering agents to provide added gastric protection in addition to the enteric coating, as well as the enteric coating and a plasticizer. The pharmaceutical composition may also include one or more lactose, sugar or starch fillers. According to the invention disclosed in this reference, when the core includes a drug which is incompatible with the enteric coating layer, an additional subcoat layer which acts as a physical barrier between the core and outer enteric coating layer is employed to prevent interaction of the acid labile drug and the acidic enteric coat. The HPMCP enteric coating starts its dissolution process at pH 5.0. The process of preparing this pharmaceutical composition requires numerous coating steps to apply the subcoat and then the enteric coat.

U.S. Pat. No. 5,026,560 discloses a pharmaceutical composition and method of making said pharmaceutical composition, wherein the pharmaceutical composition comprises a Nonpareil seed core produced by coating sucrose with corn starch, spraying the core with an aqueous binder in a solution of water or ethanol and with a spraying powder containing a drug and low substituted hydroxypropylcellulose, followed by the application of an enteric coating.

U.S. Pat. No. 4,524,060 recites a slow release pharmaceutical composition which provides a sustained release composition for treating hypertensive patients, and which comprises a mixture of micronized indoramin or a pharmaceutically acceptable salt thereof, a water-channeling agent, a wetting agent, a disintegrant, the mixture being in the form of a non-compressed pellet and having an enteric coat or sustained release coat permeable to gastrointestinal juices.

U.S. Pat. No. 5,536,507 is directed to a pharmaceutical composition having a delayed release coating or enteric coatings wherein the active agent in the composition is intended for release of a predominant amount of the drug at a point near the inlet to or within the large intestine and at a pH of approximately 6.4–7.0.

Pharmaceutical compositions which include a medicament which is unstable in an acidic environment such as the stomach and which is not adequately buffered, will require an enteric protective coating to prevent release of such medicament prior to reaching the intestines.

ddI, (also known as didanosine or 2',3'-dideoxyinosine, and marketed by Bristol-Myers Squibb Co. under the brand name Videx®), is an acid labile drug which has the formula

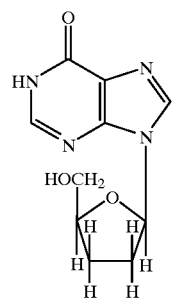

and which has been shown to be effective in the treatment of patients with the HIV virus which causes AIDS. The composition and method of inhibiting HIV replication with 2',3'-dideoxyinosine have been reported. See U.S. Pat. Nos. 4,861,759, 5,254,539 and 5,616,566, which are incorporated by reference herein. More recently, Videx® has become widely used as a component of the new therapeutic cocktails used to treat AIDS. It is also an acid labile medicament sensitive to a low pH environment and will degrade in the stomach.

Videx® is generally available in a variety of oral dosages, including Chewable/Dispersible Buffered Tablets in strengths of 25, 50, 100 or 150 mg of didanosine. Each tablet is buffered with calcium carbonate and magnesium hydroxide. Videx® tablets also contain aspartame, sorbitol, microcrystalline cellulose, Polyplasdone®, mandarin-orange flavor, and magnesium stearate. Videx® Buffered Powder for Oral Solution is supplied for oral administration in single-dose packets containing 100, 167 or 250 mg of didanosine. Packets of each product strength also contain a citrate phosphate buffer (composed of dibasic sodium phosphate, sodium citrate, and citric acid) and sucrose. A Videx® Pediatric Powder for Oral Solution is also available and which is supplied for oral administration in 4- or 8-ounce glass bottles containing 2 or 4 grams of didanosine respectively, and is to be mixed with commercial antacid before oral ingestion.

With particular emphasis on the tablets, whether ingested alone or as part of a combination ("cocktail") therapy regimen, the current chewable/dispersible buffered tablets are not conducive from a patient ease of use standpoint. Whereas the other products which are a part of the AIDS therapeutic cocktail are capsules or tablets and easily swallowed, the Videx® (referred to herein as "ddI") Chewable/Dispersible Buffered Tablets must be thoroughly chewed, manually crushed, or uniformly dispersed in water before administration. Because ddI degrades rapidly at acidic pH, ddI, in its chewable/dispersible form and its buffered powder for oral solution, contains buffering agents and is administered with antacids in the pediatric powder form. However, the presence of the large quantities of antacid components in the formulation can lead to significant GI imbalance as noted by severe diarrhea. Many patients also complain about chewing the large ddI tablets (dose=2 tablets of 2.1 g each), the taste of the ddI or the time required to disperse the tablets and the volume of fluid (4 oz) required for the dose. All these factors, coupled with the fact that other nucleoside analog drugs are marketed in a more convenient dosage presentation (i.e. capsule or smaller tablets), necessitate the development of an innovative dosage form of ddI which is easy to swallow and does not cause discomforting side effects.

Accordingly, there is provided a tablet comprising a medicament core and having a coating which prevents release of the medicament in the stomach and allows for release of the drug in the small intestine thereby eliminating the need for an antacid which may cause GI imbalance upon chronic use. Thus, pharmaceutical compositions which include a medicament which is unstable in an acid environment such as the stomach will require such a protective coating to prevent release of such medicament prior to reaching the intestines.

DESCRIPTION OF THE INVENTION

In accordance with the present invention, an enteric coated, high drug load pharmaceutical composition, and a method of making said pharmaceutical composition, is provided which includes a medicament which may degrade in a low pH environment but which is protected from doing so by the enteric coating. The pharmaceutical composition of the invention, which is advantageously in the form of tablets, includes a core which comprises a medicament, such as ddI, which is sensitive to a low pH environment and optionally a binder or filler, a disintegrant or swelling agent, and a lubricant. The core further comprises an enteric coating surrounding the core which includes a methacrylic acid copolymer and a plasticizer.

The novel enteric coated pharmaceutical of the invention will provide for protection of the medicament or therapeutically active agent, such as ddI, at pH's less than 3 (such as found in the stomach) but will permit drug release at a pH of 4.5 or higher (such as found in the upper intestines).

Accordingly, the pharmaceutical composition of the invention will usually include drugs which are chemically unstable in acidic environments. The pharmaceutical composition of the invention provides excellent protection in very acidic environments (pH<3) while not delaying the rapid release in regions of pH greater than 4, whether this be the upper intestine or the duodenum.

Most of the enteric coating materials known in the art are acidic in nature and hence may cause chemical instability when in contact with acid labile ingredients. This is especially true under high temperature and humid conditions experienced during an aqueous coating process. To minimize this acid caused instability, a protective coat or subcoat is usually applied between the particles, beadlets, pellets, tablets, etc., and the enteric coat. This protective coat physically separates the acid labile drug from the acidic enteric coat, and hence improves stability of the formulation. The process of applying such a subcoat, however, often entails multiple burdensome and time-consuming steps. Furthermore, the subcoat can cause a delay in drug release.

A process is thus described by which tablets, beadlets, pellets, and/or particles containing acid labile drugs can be successfully aqueous enteric coated without application of the protective coat or subcoat. This process involves raising the pH of the enteric coating suspension solution by using alkalizing agents. The pH of the coating suspension is raised below the point where enteric integrity of the polymer could be lost. The process may also involve the inclusion of binders, such as sodium carboxymethylcellulose, fillers, such as microcrystalline cellulose, disintegrants, such as sodium starch glycolate, and other excipients, such as magnesium oxide, which are relatively alkaline in nature, in the formulations of cores intended for enteric coating. Raising the pH of the coating suspension provides a more stable composition for the acid labile drug in the core. As a result, there is no incompatibility and no need for a protective subcoat between the acid labile drug and the acidic enteric coat. This process not only eliminates the costly additional subcoating step, but allows quicker release of the drug since the added subcoat layer delays drug release.

The process of the present invention illustrates the preparation of high (up to 99.5%) potency (uncoated) tablets, for acid labile drugs, such as ddI, using an aqueous process. No specialized equipment is required as conventional blending, compacting, tableting, and coating equipment was found to be adequate for tablet formation and coating.

In the digestive tract, the coated tablets pass through the stomach first. The transit time for the stomach is approximately two hours and the pH of this region is approximately 1 to 3. The enteric coating component allows the medicament core to remain substantially intact and thus prevents the pharmacologically active substance from being released in this region or the acid from penetrating through to the tablet core. The tablets then pass through the small intestine wherein the majority of the enteric coating component will dissolve and release the pharmacologically active substance therein. In normal flow direction therethrough, the small intestine consists of the duodenum, jejunum and ileum. Transit time through the small intestine is approximately 2–4 hours and the pH of these regions is approximately 5 to approximately 7.2.

As used herein "enteric coating", is a polymer material or materials which encase the medicament core. The polymeric enteric coating material in the present invention does not contain any active compound, i.e. any therapeutically active agent, of the present invention. Preferably, a substantial amount or all of the enteric polymer coating material is dissolved before the medicament or therapeutically active agent is released from the dosage form, so as to achieve delayed dissolution of the medicament core. A suitable pH-sensitive polymer is one which will dissolve in intestinal juices at the higher pH levels (pH greater than 4.5), such as within the small intestine and therefore permit release of the pharmacologically active substance in the regions of the small intestine and not in the upper portion of the GI tract, such as the stomach.

The polymer coating material is selected such that the therapeutically active agent will be released when the dosage form reaches the small intestine or a region in which the pH is greater than pH 4.5. Preferred coating pH-sensitive materials, which remain intact in the lower pH environs of the stomach, but which disintegrate or dissolve at the pH commonly found in the small intestine of the patient. The enteric polymer coating material begins to dissolve in an aqueous solution at pH between about 4.5 to about 5.5. The pH-solubility behavior of the enteric polymers of the present invention are such that significant dissolution of the enteric polymer coating will not occur until the dosage form has emptied from the stomach. The pH of the small intestine gradually increases from about 4.5 to about 6.5 in the duodenal bulb to about 7.2 in the distal portions of the small intestine (ileum). In order to provide predictable dissolution corresponding to the small intestine transit time of about 3 hours and permit reproducible release therein, the coating should begin to dissolve within the pH range of the duodenum and continue to dissolve at the pH range within the small intestine. Therefore, the amount of enteric polymer coating should be such that it is substantially dissolved during the approximate three hour transit time within the small intestine.

The pharmaceutical medicament present in the core will be an acid labile drug such as ddI, pravastatin, erythromycin, digoxin, pancreatin, ddA, (2',3'-dideoxyadenosine) ddC, (2',3'-dideoxycytosine) and the like. The present invention is not limited to these drugs and other drugs may be used as well. The invention is particularly adapted to pharmaceutical compositions, such as tablets, which contain ddI as the medicament. ddI will be present in an amount of about up to about 95% of the composition in the coated tablets.

One or more binders or fillers may be present in the core. Microcrystalline cellulose (PH-101) is the preferred binder most suitable for use herein. Examples of other binders which may be used include sodium carboxymethylcellulose Avicel™ PH101, Avicel™ RC 591, Avicel™ CL-611, (FMC Corp), Ceolus™ (FMC Corp.), ProSolv™ (Edward Mendell Co.) Methocel™ E-5 (Dow Corp.), Starch 1500 (Colorcon, Ltd.), Hydroxypropyl Methylcellulose (HPMC) (Shin-Etsu Chemical Co., Ltd.), Polyvinylpyrrolidone, Potassium Alginate and Sodium Alginate.

The core of the composition of the invention may also include one or more disintegrants or swelling agents, such as sodium starch glycolate marketed under the trademark EXPLOTAB (Edward Mendell Co.), Ac-Di-Sol (cross-linked sodium carboxymethylcellulose) (FMC Corp), croscarmellose sodium, corn starch, or cross linked polyvinylpyrrolidone. A lubricant such as magnesium stearate, may also be used in the preparation of the uncoated tablet, specifically as a lubricant for the compaction and tableting process.

The core employed in the pharmaceutical composition of the invention will be formed of a tablet, preferably a round, biconvex tablet, approximately 3/16 of an inch. The invention is not, however, limited in the size of the tablet and tablets of varying sizes may be made. Smaller sized tablets are advantageous, however, since they pass through the stomach with more ease than larger sized tablets. Experimentation has shown that the tablet of the present invention having core comprising ddI as the medicament, has the same bioavailability as the beadlet disclosed in co-pending U.S. Application Ser. No. 09/083,597, which was filed on May 22, 1998. Depending upon the size of the tablets, they may be ingested individually, or a plurality of tablets sufficient to attain a particular dosage may be encapsulated in a dissolvable capsule.

In an alternative embodiment of the present invention, the core can be prepared from a wet granulation process, using any of the wet granulation binders (if necessary) commonly used in the art, such as pregelatinized starch, polyvinylpyrrolidone, HPMC sodium carboxymethycellulose, potassium or sodium alginate. The wet granulation process comprises the steps of preparing granules suitable for tableting by blending a mixture comprising the medicament, a binder, and optionally, a disintegrant and filler; adding a predetermined amount of water or granulation solvent to form a wet mass blend; sizing the wet mass blend into granules to aid drying; drying the wet granules to remove excess moisture; sizing the dried granules into granules suitable for tableting, and adding lubricant, one or more fillers, one or more dry binders, optionally a disintegrant, and other excipients necessary for tableting the granules.

The enteric coating according to the present invention will include methacrylic acid copolymer, a plasticizer, and a sufficient quantity of NaOH to adjust the pH of the suspension. Other alkalizing agents, such as potassium hydroxide, calcium carbonate, sodium carboxymethylcellulose, magnesium oxide, and magnesium hydroxide can also be used.

In forming the enteric coated pharmaceutical composition of the invention, an enteric coating solution of Eudragit L-30-D 55 will be employed. Eudragit L-30-D 55 is an aqueous acrylic resin dispersion, an anionic copolymer derived from methacrylic acid and ethyl acrylate with a ratio of free carboxyl groups to the ester of approximately 1:1, and a mean molecular weight of approximately 250,000, is supplied as an aqueous dispersion containing 30% w/w of dry lacquer substance, and is marketed by Rohm-Pharma Co., Germany. As an aqueous-based coating, no dangerous or environmentally harmful organic solvents are utilized.

Although Eudragit L-30-D-55 is the preferred coating polymer, the invention is not limited in this respect and other enteric coating polymers known in the art, such as hydroxypropyl methylcellulose phthalate HP50 (HPMCP-HP50) (USP/NF 220824), HP55 (HPMCP-HP55)(USP/NF type 200731) and HP55S available from Shin Etsu Chemical, Coateric™ (polyvinyl acetate phthalate)(Colorcon Ltd.), Sureteric™ (polyvinyl acetate phthalate)(Colorcon, Ltd.), or Aquateric™ (cellulose acetate phthalate)(FMC Corp.), and the like may be employed The enteric coating will also preferably contain a plasticizer which is preferably diethyl phthalate, although the invention is not limited in this respect and other plasticizers may be used such as triethyl citrate (Citroflex-2), triacetin, tributyl sebecate, or polyethylene glycol.

The enteric coating employed in the present invention is substantially easier to process than previously reported coating systems, and is especially advantageous for coating small diameter, low mass particles (tablets) with minimal processing problems (sticking/picking) without the need for organic solvents.

In general, where the core includes a drug which is incompatible with the enteric coating layer, a subcoat layer which may be comprised of one or more film-formers or plasticizers, and which acts as a physical barrier between the core and the outer enteric coating layer will be employed. However, unlike previously reported coatings such as that disclosed in U.S. Pat. No. 5,225,202, the novel pharmaceutical composition of the present invention, as a result of the novel process utilized in making the composition of the present invention and the pH adjustment of the coating, does not require a subcoat since the need for such an insulating layer is eliminated by raising the pH of the aqueous coating suspension. Since the coating is designed to breakdown at pH 5.5, the enteric coating applied at pH 5 permits relatively rapid breakdown in the intestine as only a small amount of additional alkalinity is required to bring the pH to 5.5.

A preferred formulation for preparing a 50 mg uncoated tablet is set out below.

| Material | Amount (mg) per Tablet |
|---|---|
| TABLET CORE | |
| Drug (didanosine) | 50.00 |
| Microcrystalline Cellulose | 17.00 |
| Na Starch Glycolate | 2.10 |
| Magnesium Stearate (for compaction) | 0.60 |
| Magnesium Stearate (for tableting) | 0.30 |
| Uncoated Tablet Net Weight | 70.00 |

A preferred formulation for the preparation of an enteric film coating suspension to coat the uncoated 50 mg tablets is set out below.

| Material | Amount (g) per 100 g |
|---|---|
| COATING | |
| Eudragit L-30-D 55 | 66.67 |
| Diethyl Phthalate | 3.00 |
| Purified Water | qs |
| (pH adjusted to 5 ± 0.1 with NaOH solution) | |

The percentage range of the ingredients in the above formulations for the uncoated tablet and the enteric film coating is set forth in the following chart:

| Material | % (range) |
|---|---|
| CORE | |
| Drug (didanosine) | 1–100 |
| Microcrystalline Cellulose | 0–40 |
| Na Starch Glycolate | 0–6 |
| Magnesium Stearate | 0–3 |
| COATING | |
| Eudragit L-30-D 55 | 2–30 |
| Diethyl Phthalate | 0.5–6.0 |

The enteric coated pharmaceutical composition in the form of tablets may be prepared by a process which comprises the steps of mixing an acid labile medicament, a binder/filler, such as microcrystalline cellulose, a disintegrant, such as sodium starch glycolate, and a first portion of a lubricant, such as magnesium stearate, for compaction, in a tumbling type blender, to prepare a dry blend. The blend is then screened and placed back in the blender for a second blending. The resulting blend is slugged or compacted and then sized to form small granules. A second portion of magnesium stearate lubricant for tableting is then calculated and blended in the tumbling type blender with the screened granules. The resulting blend is then formed into tablets (uncoated) having a desired weight and hardness.

The tablets may then be coated with an enteric film coating suspension comprising Eudragit L-30-D 55 and plasticizer (diethyl phthalate), using a fluid bed coating apparatus with top spray mode, such as an Aeromatic STREA-1 table top unit, and then dried. During preparation of the film coating suspension, a NaOH solution is added to the suspension until a pH of 5.0±0.1 is obtained. Adjustment of the enteric film coating suspension to pH 5 eliminates the need for a subcoat or insulating layer. The advantage here is that an enteric coating at pH 5 permits relatively rapid breakdown in the intestine since only a small amount of alkalinity is required to bring the pH to 5.5. The suspension pH adjustment to 5±0.1 is not critical. The pH could be adjusted up to 5.4 as may be necessary of a specific formulation. Although a top spray mode fluid bed apparatus is preferred, the invention is not limited in this respect, and any suitable spray coating means, including one with a bottom spray, or a pan type coater, may also be utilized.

Depending on their size, the tablets may be ingested individually or, in another embodiment of the invention, may be filled into dissolvable, hard shell capsules, such as gelatin capsules of varying sizes depending on the dosage of medicament desired. If the tablets are to be encapsulated, a hydrophobic anti-adherent, such as talc, is added (range 0.1 to 4% by weight) to the film coated tablets and blended.

The Examples represent preferred embodiments of the present invention. The following examples further describe the materials and methods used in carrying out the invention and are intended to be for illustrative purposes only, and are not intended to limit the scope or spirit of this invention or the claims in any way. All temperatures are expressed in degrees Centigrade unless otherwise indicated and all mesh sizes are U.S. standard ASTM.

EXAMPLE 1

A ddI formulation for 50mg tablets having the following composition was prepared as described below.

EXAMPLE 1
A ddI formulation for 50 mg tablets having the following composition was prepared as described below.

| COMPOSITION | WEIGHT % OF COMPONENT | WEIGHT % OF FINAL FORMULATION |
|---|---|---|
| A: TABLET CORE | | |
| ddI | 71.4 | 65.763 |
| Microcrystalline Cellulose | 24.3 | 22.359 |
| Na Starch Glycolate | 3.0 | 2.762 |
| Magnesium Stearate | 1.3 | 1.184 |

-continued

EXAMPLE 1
A ddI formulation for 50 mg tablets having the following composition was prepared as described below.

| COMPOSITION | WEIGHT % OF COMPONENT | WEIGHT % OF FINAL FORMULATION |
|---|---|---|
| B: COATING (Based on 8% coat) | | |
| Eudragit L-30-D 55 (dry basis) | 87 | 6.892 |
| Diethyl Phthalate | 13 | 1.039 |
| (pH adjusted to 5.0 ± 0.1) | | |

The preparation of ddI tablets was commenced by adding ddI, microcrystalline cellulose, sodium starch glycolate and a first portion of magnesium stearate for compaction, into a tumbling type blender . The ingredients were blended for 10±2 minutes. Prior to blending, any of the initial ingredients which were lumpy, were passed through a #20 mesh screen.

The blended mixture was then passed through a #40 size mesh screen and re-placed into the tumbling type blender and blended again for 10±2 minutes. The resulting blend was then slugged using a ¾" flat face punches. The slugs were then passed through #10 and #20 size mesh screens for sizing.

A second portion of magnesium stearate needed for tableting was then calculated and placed into the tumbling type blender with the granulation prepared for the sizing of the slugs and blended for 10±2 minutes. The resulting blend was then tableted to obtain the desired tablet weight and hardness.

To prepare sufficient quantities of film coating suspension to coat the tablets, Eudragit L-30-D 55 was filtered through a #60 mesh screen to remove any lumps present therein. The filtered Eudragit was weighed and then added with stirring to a tarred vessel containing one-half the amount of water required. The mixture was continuously stirred for 5 minutes or until a uniform mixture was visually evident. With continuous stirring, diethyl phthalate was added to the vessel and stirring continued for 20 minutes or until a uniform mixture was visually evident. A pH meter was then standardized using pH 4 and pH 7 buffers. With continued stirring, a NaOH solution was added to the vessel until a pH of 5.0±0.1 was obtained. The formula weight of the coating suspension was adjusted using water and stirring was continued for an additional 10 minutes.

The tablet coating procedure utilized a fluid bed apparatus with a top spray mode and appropriate distribution plate to allow fluidization of the product (tablet) in the center.

Before coating, the tablets were pre-warmed in the coating unit to a temperature between 45–50° C. An inlet temperature of 50±2 ° C. was determined to be adequate. The spray rate was adjusted to allow uniform coating and adequate drying of the coat. An 8±0.5% weight gain due to the film coat was determined to be sufficient. After coating, the tablets were dried for approximately 10 minutes at an inlet temperature of approximately 50° C.

The so formed enteric coated ddI product was found to give excellent protection against gastric acid (at pH of 3) but had excellent release of ddI at pH's above 5.

EXAMPLE 2

A preferred 50 mg ddI formulation in the form of enteric coated tablets was prepared as described below. ddI (50.00 mg), microcrystalline cellulose (17.00 mg) sodium starch glycolate (2.10 mg) and a first portion of magnesium stearate for compaction (0.60 mg) were placed into a suitable tumbling type blender and blended for 10±2 min. Prior to blending, if any of the ingredients required delumping, they were passed through a #20 mesh screen.

The blended mixture was then passed through a #40 size mesh screen and re-placed into the tumbling type blender and blended again for 10±2 minutes. The resulting blend was then slugged using a ¾" flat face punches to obtain slugs with a weight and hardness of 1±0.2 g and 15–20 SCU, respectively. The slugs were then passed through #10 and #20 size mesh screens.

A second portion of magnesium stearate (0.3 g) for tableting was then placed into the tumbling type blender with the slugs and blended for 10±2 minutes. The resulting blend was then tableted using 3/16" round, plain, deep concave punches to the desired weight at a tablet hardness of 3–6 SCU.

A quantity of film coating suspension in an amount (g) per 100 g for coating the 50 mg ddI tablets was commenced by adding approximately 50 g of water into a suitable container having a stirring mechanism. While the water was being stirred moderately, 33.33 g Eudragit L 30 D-55 was slowly added thereto. Before adding to the water, the Eudragit L 30 D-55 was screened through a #60 size mesh screen.

With continued stirring, 1.50 g diethyl phthalate was added to the water/Eudragit mixture until the diethyl phthalate was in complete solution. While stirring, a sufficient quantity of sodium hydroxide solution (0.1 to 1N) was slowly added in order to adjust the pH of the suspension to 5.0. With continued stirring, water was added to make the formula weight, and the suspension was stirred for an additional 10 minutes.

The tablet coating procedure utilized an Aeromatic Tabletop (STREA-1) fluid bed apparatus, with top spray mode and appropriate distribution plate to allow fluidization of the product (tablet) in the center. The coating conditions utilized in the process were:

| | |
|---|---|
| Charge | 250 g |
| Heat Setting | 60° C. |
| Fan Setting | 14 |
| Inlet Temperature | 50° C. |
| Pre-heating Time | 5 min. |
| Spray rate, first 5 min. | 4 g/min. |
| Spray rate, final | 8 g/min. |
| Nozzle opening | 1.1 mm |
| Air Volume | 120 |
| Outlet Temperature | 36° C. |
| Weight gain | 8% |
| Final drying at fan setting 10 | 10 min. |

Before coating, the tablets were pre-warmed in the coating unit to a temperature between 45–50 ° C. An inlet temperature of 50±2 ° C. was determined to be adequate. The spray rate was adjusted to allow uniform coating and adequate drying of the coat. An 8±0.5% weight gain due to the film coat was determined to be sufficient. After coating, the tablets were dried for approximately 10 minutes at an inlet temperature of approximately 50° C.

The so formed enteric coated ddI product was found to provide excellent protection against gastric acid (at pH of 3) but had excellent release of ddI at pH's above 5.

What is claimed is:

1. A pharmaceutical tablet comprising a core comprising 2',3'-dideoxyinosine (ddI), a binder or filler, a disintegrant, and a lubricant, wherein said core is coated with an enteric coating comprising a methacrylic acid copolymer and a plasticizer, said enteric coating having a pH of 5.0±0.1, wherein said enteric coating imparts protection to said core so that said core is afforded protection in a pH environment of 3 or less while capable of releasing the ddl at a pH of 4.5 or higher, wherein said tablet contains no protective subcoat between the core and the enteric coating.

2. The tablet of claim 1, wherein said binder is microcrystalline cellulose, sodium carboxymethylcellulose, microcrystalline cellulose and carboxymethylcellulose sodium, hydroxypropylmethyl cellulose, pregelatinized starch, potassium alginate, or sodium alginate.

3. The tablet of claim 2, wherein the binder is microcrystalline cellulose.

4. The tablet of claim 1, wherein the lubricant is magnesium stearate.

5. The tablet of claim 1, wherein the disintegrant is sodium starch glycolate, croscarmellose sodium, corn starch, or cross-linked polyvinylpyrrolidone.

6. The tablet of claim 5, wherein the disintegrant is sodium starch glycolate.

7. The tablet of claim 1, wherein the methacrylic acid copolymer is methacrylic acid copolymer, Type C.

8. The tablet of claim 1, wherein the plasticizer is diethyl phthalate, triethyl citrate, triacetin, tributyl sebecate, or polyethylene glycol.

9. The tablet of claim 8, wherein the plasticizer is diethyl phthalate.

10. The tablet of claim 1, having the following composition:

| Material | % (range) |
| --- | --- |
| CORE | |
| ddl | 1–100 |
| Microcrystalline Cellulose | 0–40 |
| Na Starch Glycolate | 0–6 |
| Magnesium Stearate | 0–3 |
| COATING | |
| Methacrylic Acid Copolymer, Type C | 2–30 |
| Diethyl Phthalate | 0.5–6.0 |

11. A pharmaceutical tablet of claim 1, wherein said core comprises ddl in an amount in the range of from about 1 to about 99.5% by weight of said core.

12. A dissolvable capsule containing a plurality of the tablets of claim 1.

13. A process for the preparation of a pharmaceutical tablet of claim 1 comprising the steps of:
 (a) preparing a blend comprising ddl suitable for tableting;
 (b) tableting said blend into a plurality of individual tablets; and
 (c) coating said tablets.

14. The process of claim 3, wherein said preparing step comprises the steps of
 (a) blending a mixture comprised of ddl, a binder, a disintegrant, and a first portion of a lubricant;
 (b) passing said mixture through a #40 size mesh screen;
 (c) reblending said mixture;
 (d) slugging said blend and passing the formed slugs successively through #10 and 20 size mesh screens; and
 (e) adding a second portion of lubricant and re-blending.

15. The process of claim 14, wherein said mixture formed in step (c) is slugged using a ¾" flat face punch.

16. The process of claim 13, wherein said tableting step (b) is performed using 3/16" round, plain, deep concave punches to obtain tablets of the desired weight.

17. The process of claim 13, wherein said tablets have a hardness of 3–6 SCU.

18. The process of claim 13, wherein preparation of said coating comprises the steps of:
 (a) mixing a methacrylic acid copolymer with approximately half the amount of water required to attain the desired formulation;
 (b) adding a plasticizer to the mixture of step (a) and stirring until said plasticizer is in complete solution;
 (c) adding sodium hydroxide solution to adjust the pH of the mixture of step (b) to 5.0; and
 (d) while stirring the mixture of step (c) adding water in a sufficient amount to bring the mixture to its desired formula weight.

19. The process of claim 13, wherein said coating step (c) comprises the steps of:
 (a) pre-warming said tablets in a fluid bed spraying apparatus to approximately 45–50° C.;
 (b) spraying said tablets with said coating; and
 (c) drying said tablets.

20. The process of claim 14, wherein said binder is microcrystalline cellulose.

21. The process of claim 14, wherein said lubricant is magnesium steak rate.

22. The process of claim 14, wherein said disintegrant is sodium starch glycolate.

23. The process of claim 13, wherein said enteric coating comprises methacrylic acid copolymer and diethyl phthalate.

24. The process of claim 23, wherein said methacrylic acid polymer is Type C.

25. A process for the preparation of a pharmaceutical tablet of claim 1 comprising the steps of:
 (a) preparing a wet mass blend by a wet granulation process for the formation of granules for tableting;
 (b) tableting said granules into a plurality of individual tablets;
 (c) coating said tablets with an enteric coating polymer and plasticizer in an aqueous media; and
 (d) blending said coated tablets with an anti-adherent.

26. The process of claim 25, wherein said preparing step comprises the steps of:
 (a) blending a mixture comprised of a ddl, a binder, a disintegrant, and a filler;
 (b) adding a predetermined amount of water or granulation solvent to form a wet blend;
 (c) sizing said blend into granules to aid drying;
 (d) drying said granules to remove excess moisture;
 (e) sizing said dried granules into granules suitable for tableting; and
 (f) adding lubricant, disintegrant, one or more fillers, one or more binders, and other excipients for tableting said granules.

27. The process of claim 25, wherein preparation of said coating comprises the steps of:
 (a) mixing a methacrylic acid copolymer with approximately 50 g of water;
 (b) adding a plasticizer to the mixture formed in step (a) and stirring until said plasticizer is in complete solution;

(c) adding sodium hydroxide solution to adjust the pH of the mixture of step (b) to 5.0; and (d) while stirring the mixture of step (c) adding water in a sufficient amount to bring the mixture to its desired formula weight.

28. The process of claim 25, wherein said coating step (c) comprises the steps of:

(a) pre-warming said tablets in a fluid bed spraying apparatus to approximately 45–50° C.;

(b) spraying said tablets with said coating; and (c) drying said tablets.

29. The process of claim 26, wherein said binder is microcrystalline cellulose.

30. The process of claim 26, wherein said lubricant is magnesium stearate.

31. The process of claim 26, wherein said disintegrant is sodium starch glycolate.

32. The process of claim 25, wherein said enteric coating comprises methacrylic acid copolymer and diethyl phthalate.

33. The process of claim 32, wherein said methacrylic acid polymer is Type C.

34. The process of claim 25, wherein said anti-adherent is talc.

35. The process of claim 25, further comprising the step of filling said coated tablets prepared in step (d) into a capsule.

* * * * *